United States Patent
Yamauchi (10) Patent No.: US 9,480,550 B2
(45) Date of Patent: Nov. 1, 2016

(54) HIGHLY ELASTIC STENT AND PRODUCTION METHOD FOR HIGHLY ELASTIC STENT

(71) Applicants: CLINO LTD., Miyagi (JP); PIOLAX MEDICAL DEVICES, INC., Kanagawa (JP); JAPAN Medical Device Technology Co., Ltd., Okayama (JP)

(72) Inventor: Kiyoshi Yamauchi, Miyagi (JP)

(73) Assignees: CLINO LTD., Miyagi (JP); PIOLAX MEDICAL DEVICES, INC., Kanagawa (JP); JAPAN MEDICAL DEVICE TECHNOLOGY CO., LTD., Okayama (JP)

( * ) Notice: Subject to any disclaimer, the term of this patent is extended or adjusted under 35 U.S.C. 154(b) by 195 days.

(21) Appl. No.: 14/460,351

(22) Filed: Aug. 14, 2014

(65) Prior Publication Data
US 2015/0014288 A1    Jan. 15, 2015

Related U.S. Application Data

(62) Division of application No. 13/810,185, filed as application No. PCT/JP2011/066240 on Jul. 15, 2011, now abandoned.

(30) Foreign Application Priority Data

Jul. 15, 2010  (JP) .................................. 2010-160397
Dec. 28, 2010  (JP) .................................. 2010-293563

(51) Int. Cl.
*A61F 2/04* (2013.01)
*B23K 26/14* (2014.01)
(Continued)

(52) U.S. Cl.
CPC . *A61F 2/04* (2013.01); *A61F 2/82* (2013.01); *A61F 2/91* (2013.01); *B23K 26/146* (2015.10); *B23K 26/38* (2013.01); *A61F 2240/001* (2013.01); *A61F 2250/0018* (2013.01)

(58) Field of Classification Search
CPC ......... A61F 2/04; B23K 26/38; B23K 26/14; B23K 26/141
USPC ................. 219/121.69, 121.72, 121.84
See application file for complete search history.

(56) References Cited

U.S. PATENT DOCUMENTS 3,174,851 A   3/1965  Buehler et al.
6,013,854 A   1/2000  Moriuchi
(Continued)

FOREIGN PATENT DOCUMENTS

EP    1132058 A1    9/2001
EP    1304092 A1    4/2003
(Continued)

OTHER PUBLICATIONS

Japanese Office Action issued in Japanese Application No. 2012-524610 dated Apr. 28, 2015, with English Translation.
(Continued)

*Primary Examiner* — Samuel M Heinrich
(74) *Attorney, Agent, or Firm* — McDermott Will & Emery LLP (57) ABSTRACT

A highly elastic stent is made of an alloy that exhibits superelasticity at body temperature. At least a part of the highly elastic stent has such a property that load increases with displacement without exhibiting a distinct yield on a load-displacement curve obtained by a compression test and a bending test.

20 Claims, 9 Drawing Sheets

(51) Int. Cl.
*B23K 26/38* (2014.01)
*A61F 2/91* (2013.01)
*A61F 2/82* (2013.01)

(56) References Cited

U.S. PATENT DOCUMENTS

| | | | |
|---|---|---|---|
| 6,428,634 | B1 | 8/2002 | Besselink et al. |
| 6,508,803 | B1 | 1/2003 | Horikawa et al. |
| 7,622,070 | B2 * | 11/2009 | Atladottir ............... A61F 2/91 |
| | | | 219/121.67 |
| 2004/0004061 | A1 | 1/2004 | Merdan et al. |
| 2004/0006382 | A1 | 1/2004 | Sohier |
| 2006/0136037 | A1 | 6/2006 | DeBeer et al. |
| 2009/0319027 | A1 | 12/2009 | Moriuchi |
| 2011/0056350 | A1 * | 3/2011 | Gale ............... B23K 26/0823 |
| | | | 83/54 |

FOREIGN PATENT DOCUMENTS

| | | |
|---|---|---|
| JP | 5-103830 A | 4/1993 |
| JP | 05-293175 | 11/1993 |
| JP | 08-000738 | 1/1996 |
| JP | 08-196642 | 8/1996 |
| JP | 09-511281 A | 11/1997 |
| JP | 2001-164348 | 6/2001 |
| JP | 2001-187150 | 7/2001 |
| JP | 2002-522113 A | 7/2002 |
| JP | 2003-199833 A | 7/2003 |
| JP | 2003-290361 | 10/2003 |
| JP | 2004-529736 A | 9/2004 |
| JP | 2004-532715 A | 10/2004 |
| JP | 2005-080881 A | 3/2005 |
| JP | 2005-198853 A | 7/2005 |
| JP | 2006-247139 A | 9/2006 |
| JP | 2006-525081 A | 11/2006 |
| JP | 2008-113958 A | 5/2008 |
| JP | 2008-516668 | 5/2008 |
| JP | 2008-161475 | 7/2008 |
| WO | 02/102281 A1 | 12/2002 |
| WO | 2006/044147 A2 | 4/2006 |
| WO | 2007/134321 A2 | 11/2007 |

OTHER PUBLICATIONS

International Search Report issued International Application No. PCT/JP2011/066240, mailed on Oct. 11, 2011.

United States Non-Final Office Action issued in U.S. Appl. No. 13/810,185 dated May 14, 2014.

Japanese Office Action issued in Japanese Application No. JP 2012-524610 dated Feb. 2, 2016, with English Translation.

Extended European Search Report issued in European Application No. 11806909.5, dated Aug. 2, 2016.

Japanese Decision to Grant a Patent issued in Japanese Application No. 2012-524610, mailed Jul. 5, 2016, with English Translation.

* cited by examiner

| | No. | HEAT TREATMENT | STRESS ($\varepsilon=2\%$) |
|---|---|---|---|
| REFERENCE EXAMPLE | 1 | NONE | 1000 MPa |
| | 2 | 200°C*30 MIN | 800 |
| | 3 | 300°C*30 MIN | 700 |
| | 4 | 500°C*10 MIN | 500 |

|  | No. | TUBE | HEAT TREATMENT | S-S CURVE |
|---|---|---|---|---|
| EXAMPLE | 1 | φ 1.8 mm CORE METAL | 300°C*30 MIN | A |
|  | 2 | φ 6.0 mm CORE METAL | NONE | A |
|  | 3 | φ 6.0 mm CORE METAL | 300°C*30 MIN | A |
| COMPARA-TIVE EXAMPLE | 1 | φ 1.8 mm CORE METAL REMOVAL | 300°C*30 MIN | - |
|  | 2 | φ 1.8 mm CORE METAL REMOVAL | 500°C*10 MIN | B |
|  | 3 | φ 1.8 mm CORE METAL | 500°C*10 MIN | B |
|  | 4 | φ 6.0 mm CORE METAL | 500°C*10 MIN | B |

HIGHLY ELASTIC STENT AND PRODUCTION METHOD FOR HIGHLY ELASTIC STENT

RELATED APPLICATIONS

This is a Divisional application of U.S. patent application Ser. No. 13/810,185, filed Mar. 25, 2013, which is the National Phase under 35 U.S.C. §371 of International Application No. PCT/JP2011/066240, filed on Jul. 15, 2011, which in turn claims the benefit of Japanese Application No. 2010-160397, filed on Jul. 15, 2010, and Japanese Application No. 2010-293563, filed on Dec. 28, 2010, the disclosures of which applications are incorporated by reference herein.

FIELD

The disclosure relates to a highly elastic stent to be placed in a lumen of a human body or an animal, and to a method for producing the highly elastic stent.

BACKGROUND

Stent treatment is a medical technology that has been rapidly progressing in recent years. A stent refers to a mesh-shaped metal pipe that is left indwelling in a body in order to prevent a constricted portion of a blood vessel or the like from narrowing again after being expanded. A stent with a reduced diameter placed in a distal end of a catheter is introduced into the constricted portion, and then subjected to operations of releasing from the catheter and of expanding so as to be placed on an inner wall of a lumen such as the blood vessel. A constricted coronary artery that can cause a myocardial infarction or the like is expanded in a blood vessel expanding operation of inflating a balloon set on the inner wall housing the stent. This type of stent is called a balloon-expandable stent, which uses metal such as stainless alloy or cobalt-chromium alloy.

Among blood vessels connected to the brain, a carotid artery is particularly liable to arteriosclerosis and constriction. Blood clots and plaques accumulated in a constricted portion of a carotid artery flow into the brain to cause cerebral infarction. In this case, a self-expandable stent is used that expands via self-restoration as soon as being released from the catheter. The metal used therefor is a Ti—Ni superelastic alloy that excels in spring characteristics.

Shape-memory alloys including the Ti—Ni alloy are well-known for exhibiting a remarkable shape memory effect associated with a reverse transformation of a martensite transformation. The shape-memory alloys are also well-known for exhibiting a good superelasticity associated with a stress-induced martensite transformation caused by a strong deformation in a parent phase region after the reverse transformation. The superelasticity is remarkably exhibited particularly in the Ti—Ni alloy and in a Ti—Ni—X alloy (X=V, Cr, Co, Nb, or the like) among numerous shape-memory alloys.

The shape memory effect of the Ti—Ni alloy is disclosed, for example, in Patent Document 1. One of the characteristics of the Ti—Ni alloy's superelasticity is that, with the superelasticity starting to act at a reverse transformation start temperature (As temperature) of the alloy, eventually at or higher than a reverse transformation finish temperature (Af temperature) thereof, the alloy deformed by an external constraint restores an original shape thereof as soon as the external constraint is removed, and the shape recovery amount reaches approximately 7% in elongation strain. The As temperature means a shape recovery start temperature, and the Af temperature means a shape recovery finish temperature (shape recovery temperature). A differential scanning calorimeter (DSC) is often used in industry as a measuring device of a transformation temperature. The DSC enables observation of distinct exothermic and endothermic peaks before and after the transformation.

Patent Documents 2 to 4 each disclose an idea of using the Ti—Ni alloy's superelasticity for the self-expandable stent. In tension of the shape-memory alloy in the parent phase at or higher than the Af temperature, stress increases linearly with strain at first. Thereafter, in a consistent manner, the stress-induced martensite transformation occurs as an additional stress is applied, and a loading plateau region of the stress is continued until the strain increases to approximately 7%, and, also when the load is reduced, there is a similar unloading plateau region (refer, for example, to Patent Document 2). The disclosed idea makes use of the superelasticity associated with the distinct transformation. Moreover, in order to obtain a more highly elastic stent, a third element added alloy Ti—Ni—X (X=Nb, Hf, Ta, or W) is disclosed (refer, for example, to Patent Document 2).

The characteristics of the Ti—Ni alloy greatly change with the degree of cold working and heat treatment conditions. The Ti—Ni alloy can be subjected to processing treatment in which the transformation is suppressed so as to provide with a non-plateau superelasticity in which the DSC shows no distinct transformation peaks and the stress increases as the strain increases without exhibiting the plateau region. Such an alloy has been developed as a high-strength Ti—Ni alloy core material that does not have the plateau region for use in guide wires (refer, for example, to Patent Document 5 or 6).

CITATION LIST

Patent Literature

Patent Literature 1: U.S. Pat. No. 3,174,851
Patent Literature 2: Publication of Japanese Translation of PCT Application No. H9-511281
Patent Literature 3: Japanese Laid-open Patent Publication No. H8-000738
Patent Literature 4: Japanese Laid-open Patent Publication No. H8-196642
Patent Literature 5: Japanese Laid-open Patent Publication No. H5-293175
Patent Literature 6: Japanese Laid-open Patent Publication No. 2001-164348

SUMMARY

Technical Problem

A stent is a mesh-shaped metal pipe structure and is conventionally composed of braided wires. However, considerations such as compact storage characteristics, friction where the wires crossover each other that is caused by pulsation after indwelling in the body, and fretting have become obvious, and thus, the braided wire structure has been replaced with a slotted tube as production of seamless tubes has become industrialized.

The slots are processed with a laser, and the processed tube needs linearity in order to have a good uniformity of the grid.

Thus, for the self-expandable stent, heat straightening (tension annealing) has been normally preferred to be applied to the cold-worked tube of the Ti—Ni alloy, for example, at 500° C. The slotted tube processed with a laser is expanded to a diameter for indwelling in the body, and is subjected to heat treatment for shape fixation. For the shape fixation (memory processing), it is preferable to apply only once the heat treatment to a cold-worked material without transformation, and it is not preferable to apply heat treatment again to heat-treated material. For example, a coil spring is made by coiling a cold-worked wire and then by applying thereto the treatment at 400° C. to 500° C. However, the slotted stent that has undergone the heat straightening is vulnerable to self-collapse due to a rapid increase in transformation stress during the expansion and the heat treatment, and thus, needs to be expanded step by step. For example, in the case of expanding a tube of ϕ 2 mm to ϕ 6 mm, the stepwise expansion is performed five to ten times, and the heat treatment is applied at each time at 500° C.

A radial force given by the stent as an essential function thereof depends on a material stiffness, and in the case of the Ti—Ni alloy, is well represented by a yield stress or an apparent yield (strength at an elongation of 2%).

However, in the stent that has under gone the repeated heat treatment at 500° C., recrystallization of the alloy is extremely progressed, so that texture obtained by the cold working almost totally disappears, resulting in reduction in the yield stress. For this reason, in order to ensure the radial force of the stent, the stent needs to be ensured of a sufficient cross-sectional area; that is, the stent needs to be increased in wall thickness. Thus, there have been issues such as the storage characteristics and cyclic damage.

The description has been made here of the Ti—Ni alloy serving as a core of the self-expandable stent. However, also in the Co—Cr alloy and the stainless alloy each serving as a core of the balloon-expandable stent, a sufficient strength could not be obtained because a sufficient cold working rate could not be ensured when tubes containing these alloys are heat-straightened, and as a result, there has been the same problems in order to ensure the radial force.

In the case of producing the stent with the laser processing as described above, the heat straightening (tension annealing) for ensuring the linearity incurs deterioration in metal performance. In addition, it is not preferable to perform heat treatment before the heat treatment in the expansion processing.

Accordingly, there is a need to provide a highly elastic stent and a method for producing the highly elastic stent that do not cause performance deterioration even by using laser processing.

Solution to Problem

In some embodiments, a highly elastic stent is made of an alloy that exhibits superelasticity at body temperature, and at least a part of the highly elastic stent has such a property that load increases with displacement without exhibiting a distinct yield on a load-displacement curve obtained by a compression test and a bending test. Here, the term "body temperature" refers to a temperature of a living human being. The expression "without exhibiting a distinct yield" means that, for example, a load-displacement curve does not exhibit a yield point (point at which a relation between increases of displacement and load changes from a proportional relation to a relation in which only the increase of displacement becomes larger). If the yield point is not exhibited on the load-displacement curve, a proof stress point is used instead. The proof stress point is calculated on the basis of the strength when the displacement (strain) reaches 0.2%.

In some embodiments, the alloy is any of Ti—Ni alloy, Co—Cr alloy, and stainless alloy.

In some embodiments, a method for producing the highly elastic stent includes: inserting a rod-shaped core metal into a hollow portion of a tube-shaped stent base; a maintaining, as needed, linearity of the stent base with the core metal inserted therein, and thereafter, of cutting slot forming portions with a laser light while suppressing a heat effect by the laser light on a periphery of the slot forming portions so as to form slots and thus to make a stent; and removing the core metal from the stent.

Here, the expression "a heat effect by the laser light on a periphery of the slot forming portions" includes reflection of the laser light to the periphery of the slot forming portions, scattering of the laser light to the periphery of the slot forming portions, melting of the core metal in the periphery of the slot forming portions, and welding of the stent base and the core metal in the periphery of the slot forming portions.

In some embodiments, the method further includes expanding the stent from which the core metal has been removed to a predetermined diameter while performing heat treatment on the stent at 350° C. or below.

In some embodiments, the slots are formed by cutting the slot forming portions with a laser that uses a water jet, which is formed so as to reach the stent base, as a waveguide of the laser light.

Advantageous Effects of Invention

According to some embodiments, at least a part of a highly elastic stent has such a property that load increases with displacement without exhibiting a distinct yield on a load-displacement curve obtained by a compression test and a bending test. Therefore, existing characteristics can be maintained even if thinning is carried out, and consequently, it is possible to achieve excellent storage characteristics and repeated use, thus excellent durability. Accordingly, laser processing does not cause performance deterioration.

According to some embodiments, a method for producing the highly elastic stent includes inserting a rod-shaped core metal into a hollow portion of a stent base, maintaining, as needed, linearity of the stent base with the core metal inserted therein, and thereafter, cutting slot forming portions with a laser light while suppressing a heat effect by the laser light on a periphery of the slot forming portions so as to form slots and thus to make a stent, and removing the core metal from the stent. Therefore, the highly elastic stent has such a property that load increases with displacement without exhibiting a distinct yield on a load-displacement curve obtained by a compression test and a bending test, in the same manner as a stress-strain curve in tension of a wire rod made of an alloy that exhibits superelasticity at body temperature. As a result, the existing characteristics can be maintained even if thinning is carried out. Therefore, it is possible to produce the highly elastic stent that excels in storage characteristics, and that can be repeatedly used and thus excels in durability. Consequently, performing the laser processing on the tube-shaped stent base does not cause performance deterioration.

DESCRIPTION OF EMBODIMENTS

A preferred embodiment of a highly elastic stent and a method for producing the highly elastic stent according to the present invention will be described below in detail with reference to the accompanying drawings.

FIGS. 1A to 1D are explanatory diagrams schematically illustrating a part of the method for producing the highly elastic stent according to an embodiment of the present invention. Here, the method for producing the highly elastic stent includes an insertion step, a tube drawing step, a holding step, a cutting step, and a removal step.

Figure 1A:
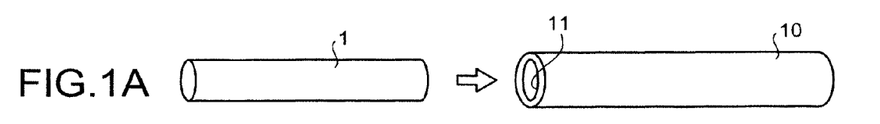
FIGS. 1A to 1D are explanatory diagrams schematically illustrating a part of a method for producing a highly elastic stent according to an embodiment of the present invention.

The insertion step is, as illustrated in FIG. 1A, a step of inserting a rod-shaped core metal 1 made of steel into a hollow portion 11 of a tube-shaped stent base 10 having, for example, a Ti—Ni alloy as a core (core material). Here, the stent base 10 is formed by performing hot processing, machining process, and rolling processing on, for example, a Ti—Ni alloy ingot. The core metal 1 has a size with an outside diameter nearly fitting to an inside diameter of the stent base 10.

Figure 1B:
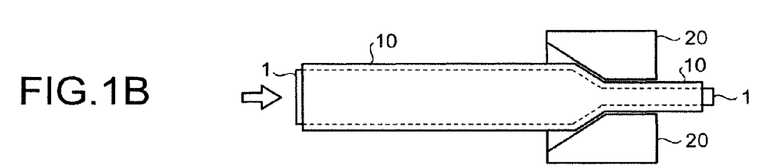

The tube drawing step is, as illustrated in FIG. 1B, a step of shrinking, with a die 20 or the like, the diameter of the stent base 10 with the core metal 1 inserted therein so as to lengthen the overall length of the stent base 10. After the tube drawing step as described above, the stent base 10 may be cut to a desired length.

Figure 1C:
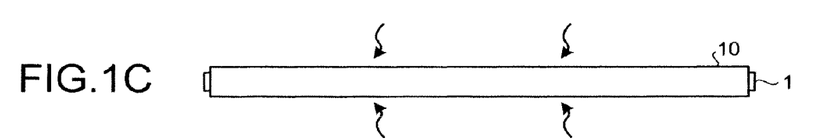

The holding step is, as illustrated in FIG. 1C, a step of applying heat treatment to the stent base 10 drawn at the tube drawing step for a predetermined time at a desired temperature while holding the stent base 10 in a linear state. Here, if the core of the stent base 10 is a Ti—Ni alloy, the heat treatment is preferably applied for approximately 30 minutes at approximately 300° C. Note that, in the production method in accordance with the present embodiment, the holding step is not an essential step, but a step performed as necessary. Compared with a case of applying heat treatment at approximately 500° C. like in the case of conventional heat straightening, applying the heat treatment at approximately 300° C. as described at the holding step above does not cause deterioration of metal, and may not have an adverse effect at a subsequent expansion processing step.

Figure 1D:
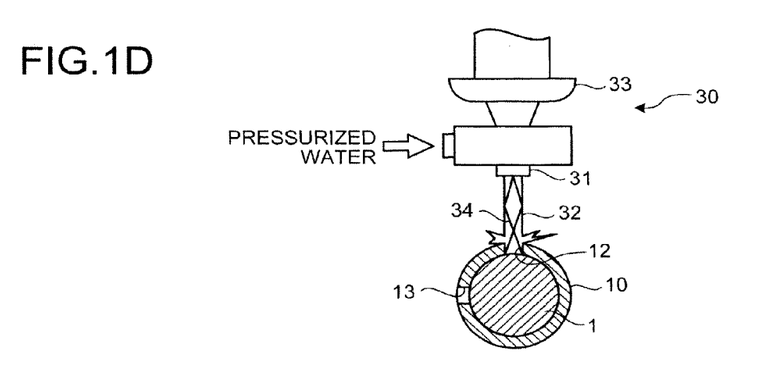

The cutting step is, as illustrated in FIG. 1D, a step of forming slots 13 by cutting slot forming portions 12 of the stent base 10 with, for example, a laser 30 that uses a water jet as a waveguide of a laser light, such as referred to as water laser. Here, the water laser 30 injects pressurized water from a nozzle 31 to form a water jet 32 reaching the stent base 10 serving as a target object, and irradiates the slot forming portions 12 with the laser light 34 that passes through a lens 33 and is emitted from the nozzle 31 while being reflected in the water jet 32, so as to cut the slot forming portions 12. With the water laser 30 described above, it is possible to cut the slot forming portions 12 with the laser light 34 while suppressing a heat effect by reflection, scattering, and the like of the laser light 34 on a periphery of the slot forming portions 12 and cooling the slot forming portions 12; in other words, it is possible to form the slots 13 by cutting desired portions of the stent base 10 with the core metal 1 inserted therein.

Note that the water laser 30 is cited here as an example. However, not limited to such a water laser 30, any type of laser light 34 can be applied to the present invention if the laser light 34 can cut the slot forming portions 12 while suppressing the heat effects by the laser light 34 on the periphery of the slot forming portions 12. For example, a pulsed laser can be used.

Figure 2A:
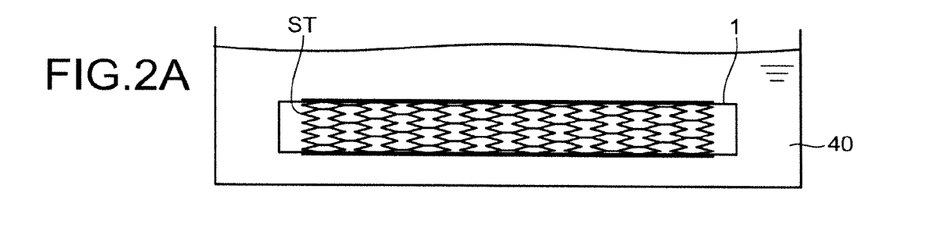
FIGS. 2A to 2C are explanatory diagrams schematically illustrating a removal step performed after the steps illustrated in FIGS. 1A to 1D.
Figure 2B:
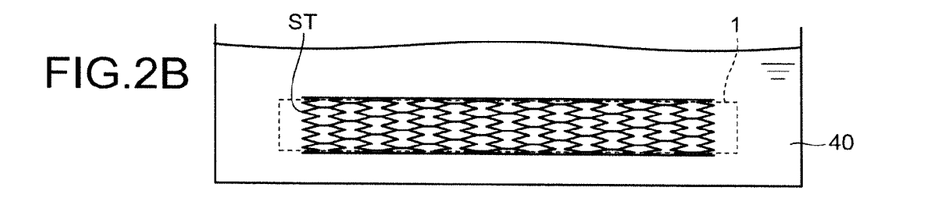
Figure 2C:
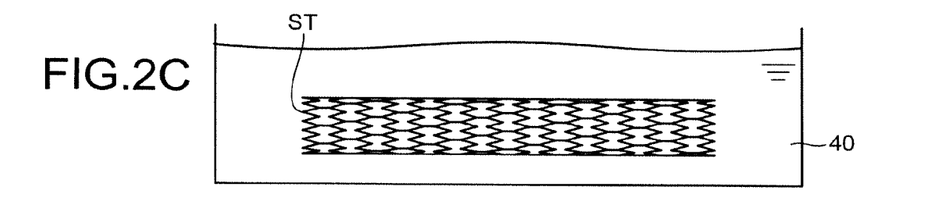

FIGS. 2A to 2C are explanatory diagrams schematically illustrating the removal step performed after the steps illustrated in FIGS. 1A to 1D. The removal step is a step of removing the core metal 1 from a stent ST that has been obtained by forming the slots 13 in the stent base 10.

Figure 3:
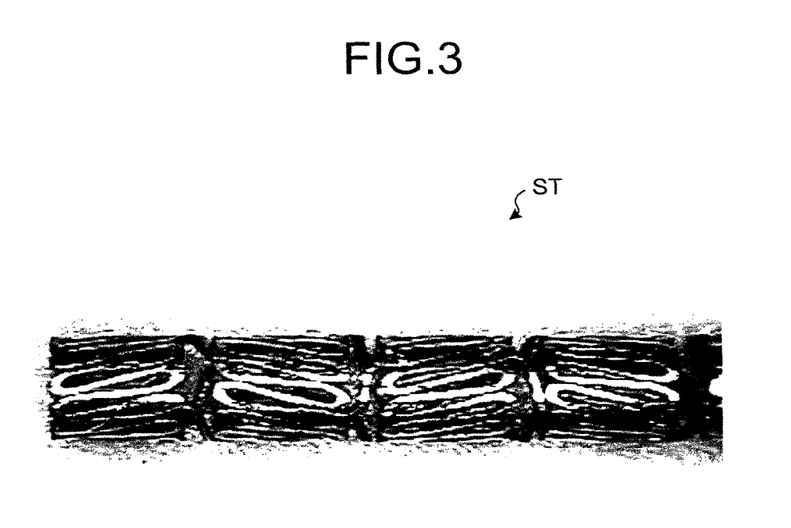
FIG. 3 is a view illustrating the highly elastic stent after the removal step.

In the removal step as described above, as illustrated in FIG. 2A, the stent ST with the core metal 1 inserted therein is immersed in a chemical treatment liquid 40 such as a nitric acid solution. Then, as illustrated in FIG. 2B, the core metal 1 is dissolved. Thereafter, as illustrated in FIG. 2C, the core metal 1 is removed. As a result, the stent ST illustrated in FIG. 3 is obtained.

FIGS. 4A to 4D are explanatory diagrams schematically illustrating the expansion processing step performed after the removal step illustrated in FIGS. 2A to 2C. The expansion processing step is a step of expanding, to a desired diameter, the diameter of the stent ST from which the core metal 1 has been removed at the removal step, i.e., the stent ST with its diameter reduced.

Figure 4A:
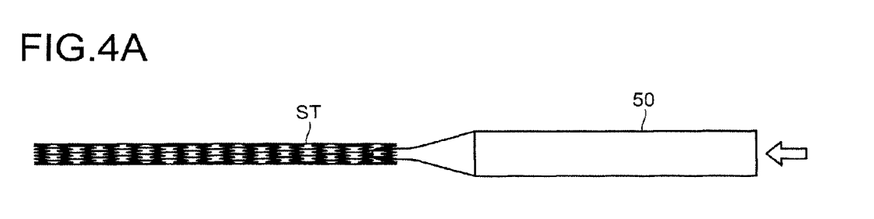
FIGS. 4A to 4D are explanatory diagrams schematically illustrating an expansion processing step performed after the removal step illustrated in FIGS. 2A to 2C.
Figure 4B:
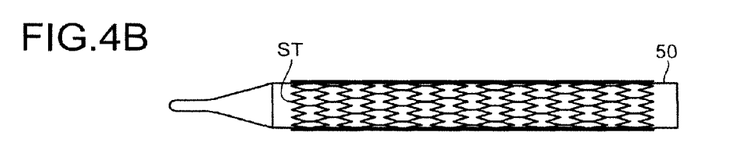
Figure 4C:
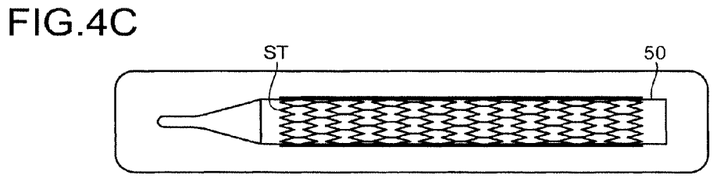
Figure 4D:
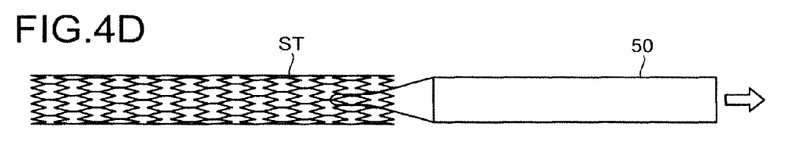
Figure 5:
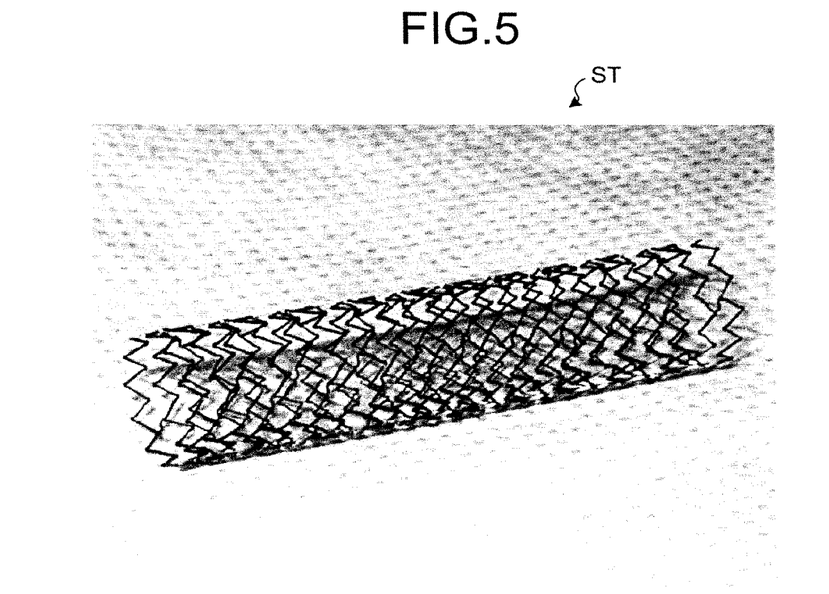
FIG. 5 is a view illustrating the highly elastic stent after the expansion processing step.

In the expansion processing step, as illustrated in FIG. 4A, a jig 50 having a tapered shape at an end thereof is inserted into the hollow portion of the stent ST with its diameter reduced. As a result, as illustrated in FIG. 4B, the stent ST is placed in a state with its diameter expanded so as to have an inside diameter fitting to the outside diameter of the jig 50. The stent ST with its diameter expanded by inserting therein the jig 50 as described above is placed under a thermal atmosphere of, for example, 350° C. or below, preferably 300° C. or below, as illustrated in FIG. 4C, and is subjected to heat treatment for a predetermined time. This heat treatment is applied for the purpose of shape fixation when the stent ST is expanded. After the heat treatment, as illustrated in FIG. 4D, the jig 50 is removed so as to obtain the stent ST as illustrated in FIG. 5.

The highly elastic stent ST produced by such a production method has been formed, in the production process, with the slots 13 in the stent base 10 by the laser processing in the state in which the core metal 1 is inserted in the hollow portion 11 of the stent base 10; in other words, the slots 13 have been formed by the laser processing while the linearity of the stent base 10 is maintained only with the heat treatment at 300° C. or below without performing the heat straightening by heating to 500° C. or above as in the conventional manner. Therefore, as will be clear from Examples given below, the highly elastic stent ST has such a property that load increases with displacement without exhibiting a distinct yield on load-displacement curves obtained by a compression test and a bending test, in the same manner as a stress-strain curve in tension of a wire rod made of a Ti—Ni alloy. In other words, it is possible to suppress a problem in which, like in the conventional case, recrystallization of the alloy is extremely progressed so that texture obtained by cold working almost totally disappears, and thus, a yield stress is reduced.

Accordingly, the highly elastic stent ST in accordance with the present embodiment has a high stress function, and excels in storage characteristics because existing characteristics can be maintained even if thinning is carried out. Moreover, the highly elastic stent ST can be repeatedly used, thus being excellent in durability. Therefore, applying the laser processing to the tube-shaped stent base 10 does not cause performance deterioration.

Note that, in the above-described embodiment, alloys practicable in the present invention include not only the Ti—Ni alloy, which exhibits superelasticity at body temperature of a living human being, but also Ti—Ni—X alloys and others (Cu group and Fe group alloys, etc.) with a third element added therewith, SUS, Co—Cr alloys, and Mg alloys.

Examples of the present invention will be described below.

Ti—Ni Alloy Stent

Example 1

A Ti—Ni alloy ingot that contains 51% of Ni and the remaining part consisting of Ti is formed by hot processing into a rod of $\phi$ 17 mm, and then, by machining process, into a pipe of $\phi$ 15 mm×11 mm. Thereafter, the pipe is formed by rolling processing into a size of $\phi$ 8.0 mm×$\phi$ 7.0 mm. Then, steel is inserted as the core metal (1), and wire-drawing processing is applied in the same manner as wire rod processing to form a tube (stent base (10)) of $\phi$ 1.8 mm×$\phi$ 1.4 mm with a cold working rate of 50%. After being cut into a length of approximately 2 m, the tube is formed into a linear tube with the core metal (stent base (10) with the core metal) by using a cold wire straightener (straightening with dies for wire). Thereafter, the linear tube with the core metal is heat-treated for 30 minutes at 300° C.

The heat-treated linear tube with the core metal of $\phi$ 1.8 mm is formed with the slots (13) using a laser beam machine to be made into a stent. The laser beam machine is a device in which a laser is shielded by water. Thereafter, the core metal (1) is removed from the stent by the chemical treatment (dissolution in a nitric acid solution), and after applying superelastic treatment for 30 minutes at 300° C., electrolytic grinding surface treatment is applied to obtain the stent (ST) in Example 1.

Example 2

A Ti—Ni alloy ingot that contains 51% of Ni and the remaining part consisting of Ti is formed by the hot processing into a rod of $\phi$ 17 mm, and then, by the machining process, into a pipe of $\phi$ 15 mm×2 mm. Thereafter, the pipe is processed by the rolling processing, and then by the wire-drawing processing with the core metal (1) inserted therein to be formed into a tube (stent base (10)) of $\phi$ 6.0 mm×$\phi$ 5.6 mm with a cold working rate of 30%. After being cut into a test piece of approximately 2 m, the tube is formed into a linear tube with the core metal (stent base (10) with the core metal) by using the cold wire straightener (straightening with dies for wire).

Thereafter, the linear tube with the core metal of $\phi$ 6.0 mm is formed with the slots (13) using the laser beam machine to be made into a stent. The laser beam machine is the device in which a laser is shielded by water. Thereafter, the core metal (1) is removed from the stent by the chemical treatment (dissolution in a nitric acid solution), and the electrolytic grinding surface treatment is applied to obtain the stent (ST) in Example 2. The point is that the stent in Example 2 is not heat-treated in the production process.

Example 3

A Ti—Ni alloy ingot that contains 51% of Ni and the remaining part consisting of Ti is formed by the hot processing into a rod of $\phi$ 17 mm, and then, by the machining process, into a pipe of $\phi$ 15 mm×2 mm. Thereafter, the pipe is processed by the rolling processing, and then by the wire-drawing processing with the core metal (1) inserted therein to be formed into a tube (stent base (10)) of $\phi$ 6.0 mm×$\phi$ 5.6 mm with a cold working rate of 30%. After being cut into a test piece of approximately 2 m, the tube is formed into a linear tube with the core metal (stent base (10) with the core metal) by using the cold wire straightener (straightening with dies for wire). Thereafter, the linear tube with the core metal is heat-treated for 30 minutes at 300° C.

The heat-treated linear tube with the core metal $\phi$ 6.0 mm is formed with the slots (13) using the laser beam machine to be made into a stent. The laser beam machine is the device in which a laser is shielded by water. Thereafter, the core metal (1) is removed from the stent by the chemical treatment (dissolution in a nitric acid solution), and the electrolytic grinding surface treatment is applied to obtain the stent (ST) in Example 3.

Comparative Example 1

By the same method as that of Example 1, a linear tube with the core metal of $\phi$ 1.8 mm is made, and the linear tube with the core metal is heat-treated for 30 minutes at 300° C. The core metal is removed from the heat-treated linear tube with the core metal. However, the tube from which the core metal had been removed could not maintain a sufficient linearity, and thereby could not be processed with a laser thereafter, thus failing to be formed into a stent.

Comparative Example 2

The same kind of Ti—Ni alloy ingot as that of Example 1 is formed by the hot processing into a rod of $\phi$ 17 mm, and then, by the machining process, into a pipe of $\phi$ 15 mm×11 mm. Thereafter, the pipe is formed by the rolling processing into a size of $\phi$ 8.0 mm×$\phi$ 7.0 mm. Hardened steel is inserted as the core metal into the pipe, and the removal and insertion of the core metal is repeated for each of the wire-drawing passes. Thus, the pipe is formed into a tube of $\phi$ 1.8 mm×$\phi$ 1.4 mm with a cold working rate of 50%, and cut into a length of approximately 2 m. Note that a wire drawing rate of 20% to 30% is normally preferred to be obtained from each pass. A wire drawing rate higher than that is likely to cause fracture. Thus, in Comparative Example 2, the process from $\phi$ 2.0 mm to $\phi$ 1.8 mm is performed in the last pass of the drawing. Thereafter, the tube is subjected to a heat straightening process for 10 minutes at 500° C.

The tube having undergone the heat straightening process is formed with the slots by the laser beam machine. After being subjected to the superelastic treatment for 10 minutes at 500° C. to be increased in diameter successively from φ 2.0 mm, φ 3.0 mm, φ 4.0 mm, φ 5.0 mm, up to φ 6.0 mm, the tube is subjected to the electrolytic grinding surface treatment to obtain a stent serving as Comparative Example 2.

Comparative Example 3

By the same method as that of Example 1, a tube of φ 1.8 mm×φ 1.4 mm with a cold working rate of 50% is obtained. After being cut into a length of approximately 2 m, the tube is formed into a linear tube with the core metal by using the cold wire straightener (straightening with dies for wire). Thereafter, the linear tube with the core metal is subjected to the heat straightening process for 10 minutes at 500° C.

The heat-straightened linear tube with the core metal of φ 1.8 mm is formed with the slots by the laser beam machine to be made into a stent. The laser beam machine is the device in which a laser is shielded by water. Thereafter, the core metal is removed from the stent by the chemical treatment (dissolution in a nitric acid solution). After the superelastic treatment is applied, the electrolytic grinding surface treatment is applied to obtain the stent serving as Comparative Example 3.

Comparative Example 4

By the same method as that of Example 3, a tube of φ 6.0 mm×φ 5.6 mm with a cold working rate of 30% is obtained. After being cut into a length of approximately 2 m, the tube is formed into a linear tube with the core metal by using the cold wire straightener (straightening with dies for wire). Thereafter, the linear tube with the core metal is subjected to the heat straightening process for 10 minutes at 500° C.

The heat-straightened linear tube with the core metal of φ 6.0 mm is formed with the slots by the laser beam machine to be made into a stent. The laser beam machine is the device in which a laser is shielded by water. Thereafter, the core metal is removed from the stent by the chemical treatment (dissolution in a nitric acid solution). After the superelastic treatment is applied, the electrolytic grinding surface treatment is applied to obtain the stent serving as Comparative Example 4.

Reference Example 1

A Ti—Ni alloy that contains 51% of Ni and the remaining part consisting of Ti is processed by wire-drawing processing to obtain a wire of 0.35 mm with a cold working rate of 50%. The wire is subjected to a tensile test to conduct a mechanical property evaluation (stress at a 2% elongation on the stress-strain (S-S) curve). Test materials are as follows: material cold-processed; material heat-treated for 30 minutes at 200° C.; material heat-treated for 30 minutes at 300° C.; and material heat-treated for 10 minutes at 500° C.

Figure 6:
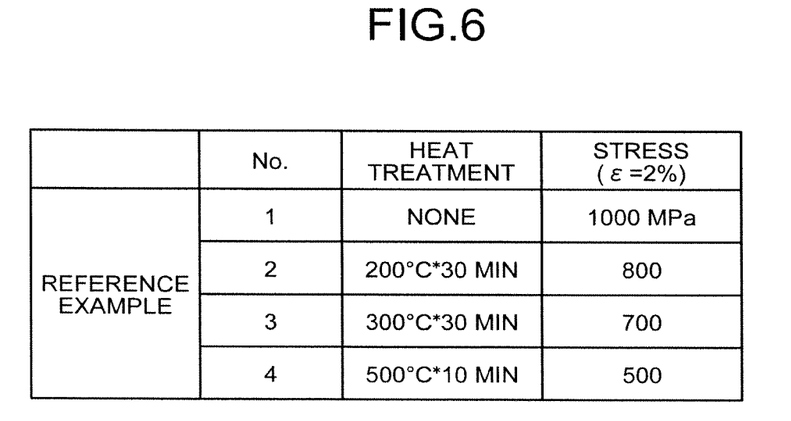
FIG. 6 is a diagram illustrating tensile test results of Reference Examples 1 to 4.
Figure 7:
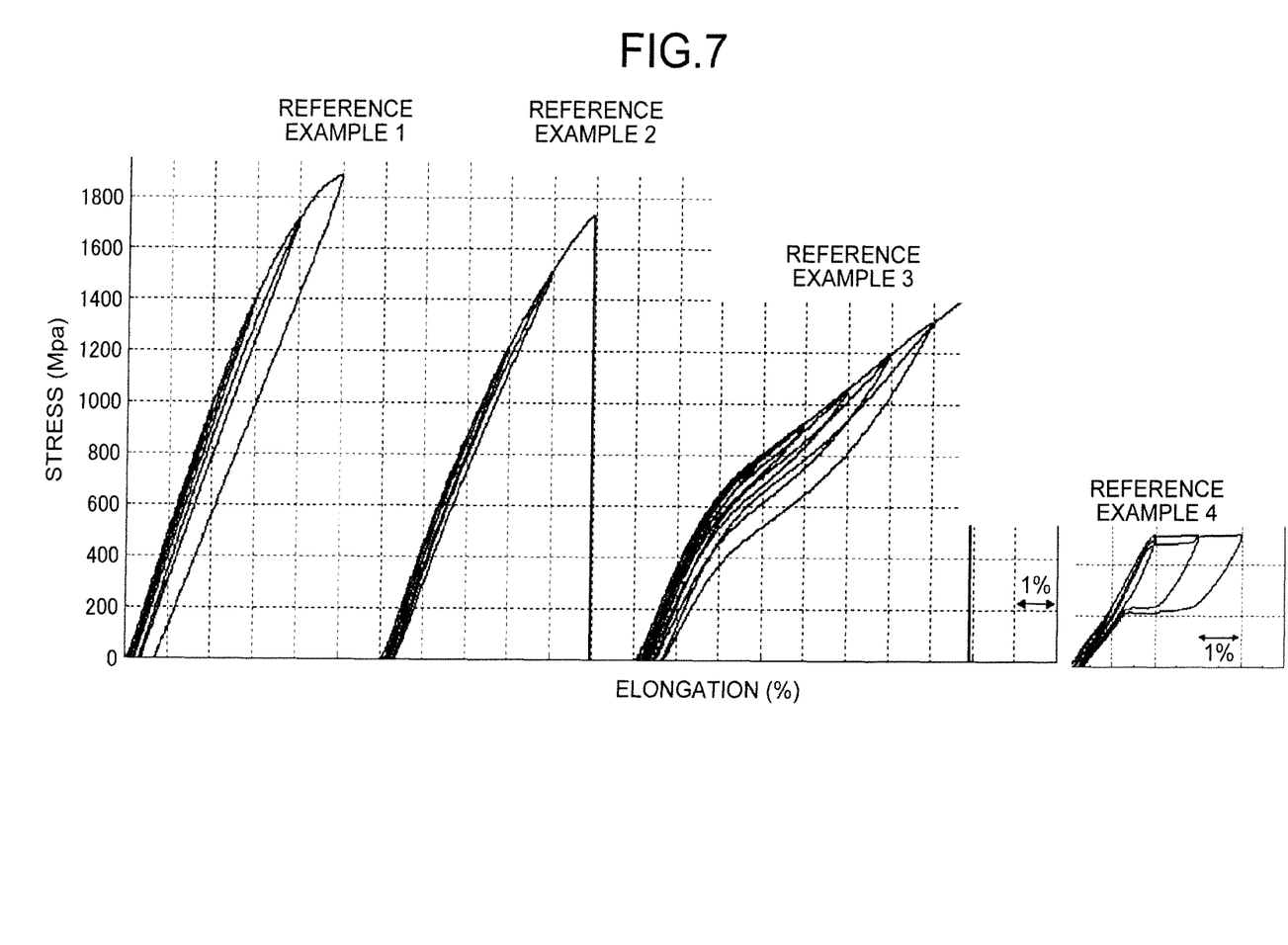
FIG. 7 is a graph illustrating S-S curves in the tensile tests of Reference Examples 1 to 4.

FIG. 7 illustrates results of the S-S curves in the tensile tests of the following test materials illustrated in FIG. 6: the cold-worked wire of 0.35 mm work-hardened (reference example 1); the material heat-treated for 30 minutes at 200° C. (reference example 2); the material heat-treated for 30 minutes at 300° C. (reference example 3); and the material heat-treated for 10 minutes at 500° C. (reference example 4).

As illustrated in FIG. 7, each of Reference Examples 1 to 3 exhibits, on each of the S-S curves, a substantially linear load change in a loading-unloading cycle without exhibiting a distinct yield, and has a slight amount of hysteresis. Reference Example 4 exhibits a distinct yield and a plateau.

Figure 8:
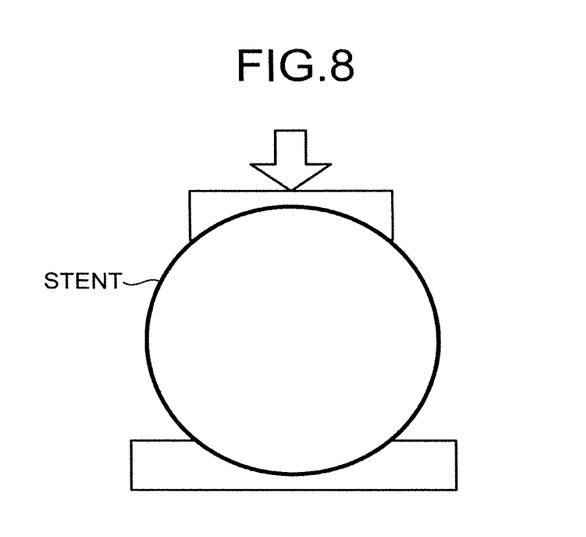
FIG. 8 is an explanatory diagram schematically illustrating a pressing tester for performing radial force evaluations.
Figure 9:
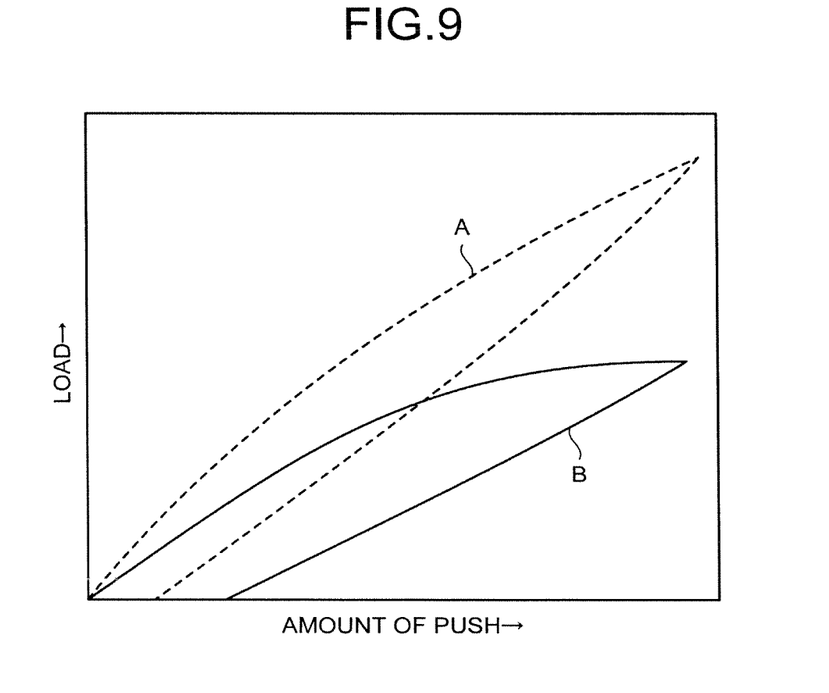
FIG. 9 is a graph illustrating test results of Examples 1 to 3 and Comparative Examples 2 to 4.
Figure 10:
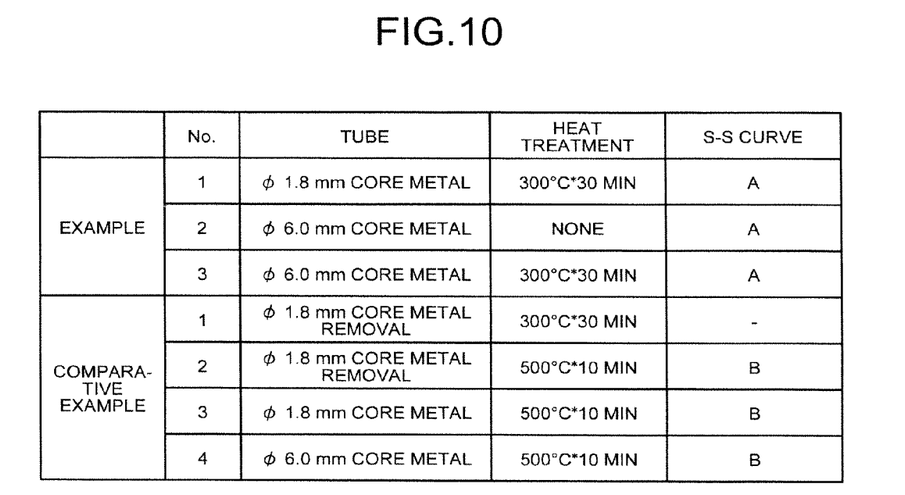
FIG. 10 is a chart summarizing test results of stents of Examples 1 to 3 and stents of Comparative Examples 1 to 4.

By conducting pressing tests as illustrated in FIG. 8, radial force evaluations are performed for the stents (stents expanded to φ 6.0 mm) of Examples 1 to 3 and for the stents (stents expanded to φ 6.0 mm) of Comparative Examples 2 to 4, which have been described above. As a result, each of the stents of Examples 1 to 3 exhibited an S-S curve such as illustrated by "A" in FIG. 9, while each of the stents of Comparative Examples 2 to 4 exhibited an S-S curve such as illustrated by "B" in FIG. 9. This means that the stents of Examples 1 to 3 exhibit tendencies similar to those of Reference Examples 1 to 3, while the stents of Comparative Examples 2 to 4 exhibit tendencies similar to that of Reference Example 4. FIG. 10 illustrates a summary of these results.

From the description given above, it is obvious that each of the stents of Examples 1 to 3 has such a property that load increases with displacement without exhibiting a distinct yield on each of the load-displacement curves obtained by the compression test and the bending test, in the same manner as the stress-strain curve in tension of the wire rod made of the Ti—Ni alloy.

Co—Cr Alloy Stent

Example 4

A Co—Cr alloy ingot is formed by the hot processing into a rod of φ 17 mm, and then, by the machining process, into a pipe of φ 15 mm×11 mm. Thereafter, the pipe is formed by the rolling processing into a size of φ 8.0 mm×φ 7.0 mm. Then, steel is inserted as the core metal (1), and the wire-drawing processing is applied in the same manner as the wire rod processing to form a tube (stent base (10)) of φ 1.8 mm×φ 1.4 mm with a cold working rate of 50%. After being cut into a length of approximately 2 m, the tube is formed into a linear tube with the core metal (stent base (10) with the core metal) by using the cold wire straightener (straightening with dies for wire).

The linear tube with the core metal is formed with the slots (13) using the laser beam machine to be made into a stent. The laser beam machine is the device in which a laser is shielded by water. Thereafter, the core metal (1) is removed from the stent by the chemical treatment (dissolution in a nitric acid solution), and the electrolytic grinding surface treatment is applied to obtain the stent (ST) in Example 4.

Comparative Example 5

By the same method as that of Example 4, a linear tube with the core metal of φ 1.8 mm is obtained. The linear tube with the core metal is formed with the slots by the laser beam machine to be made into a stent. The laser beam machine is the device in which a laser is shielded by water. Thereafter, the core metal is removed from the stent by the chemical treatment (dissolution in a nitric acid solution). After the heat treatment at 800° C. is applied, the electrolytic grinding surface treatment is applied to obtain the stent serving as Comparative Example 5.

Reference Example 2

Figure 11:
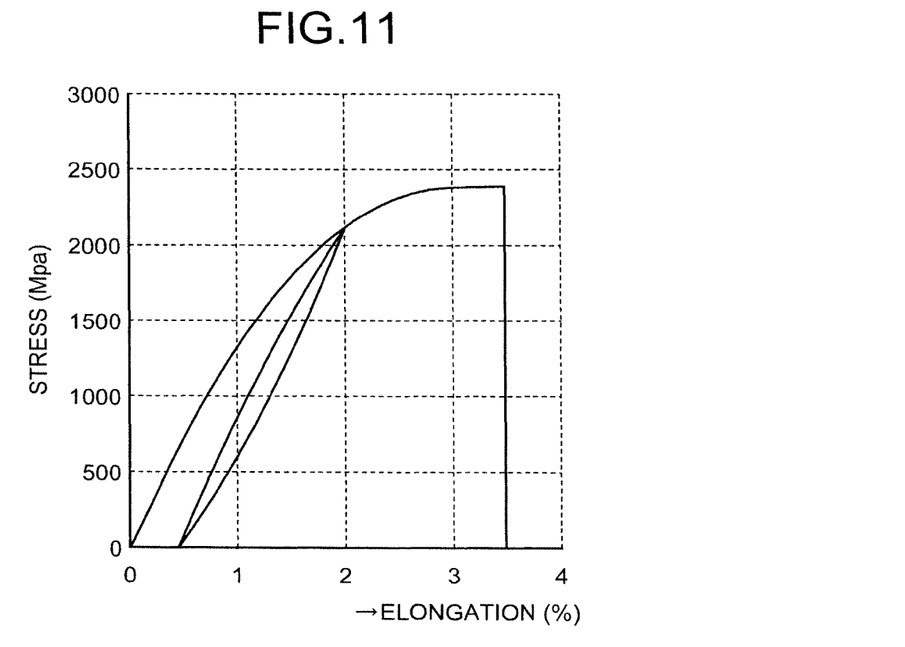
FIG. 11 is a graph illustrating an S-S curve of a tensile test result of Reference Example 5.
Figure 12:
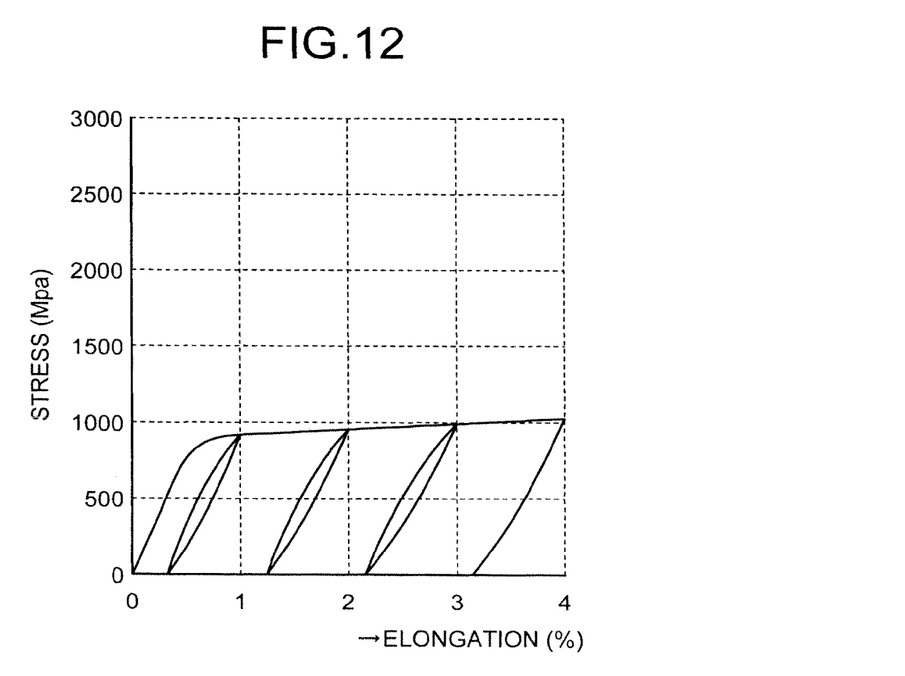
FIG. 12 is a graph illustrating an S-S curve of a tensile test result of Reference Example 6.

A Co—Cr alloy (for industrial use) is processed by the wire-drawing processing to obtain a wire of φ 0.2 mm with a cold working rate of 95%. The wire is subjected to the tensile test to conduct the mechanical property evaluation (stress at a 2% elongation on the stress-strain (S-S) curve). Test materials are material cold-processed (reference example 5) and material heat-treated at 800° C. (reference example 6). FIG. 11 illustrates S-S curves of Reference Example 5, and FIG. 12 illustrates S-S curves of Reference Example 6. As illustrated in FIG. 11, Reference Example 5 exhibits, on each of the S-S curves, a substantially linear load change in a loading-unloading cycle without exhibiting a distinct yield, and has a slight amount of hysteresis. As illustrated in FIG. 12, Reference Example 6 exhibits a distinct yield and a plateau.

By conducting the pressing tests as illustrated in FIG. 8, the radial force evaluations are performed for the stent of Example 4 and for the stent of Comparative Example 5, which have been described above. As a result, the stent of Example 4 exhibited an S-S curve similar to that illustrated in FIG. 11, while the stent of Comparative Example 5 exhibited an S-S curve similar to that illustrated in FIG. 12. This means that the stent of Example 4 exhibits a tendency similar to that of Reference Example 5, while the stent of Comparative Example 5 exhibits a tendency similar to that of Reference Example 6.

From the description given above, it is obvious that the stent of Example 4 has such a property that load increases with displacement without exhibiting a distinct yield on each of the load-displacement curves obtained by the compression test and the bending test, in the same manner as the stress-strain curve in tension of the wire rod made of a Co—Cr alloy.

REFERENCE SIGNS LIST

1 Core metal
10 Stent base
ST Stent
11 Hollow portion
12 Slot forming portion
13 Slot
20 Die
30 Water laser
31 Nozzle
32 Water jet
33 Lens
34 Laser light
40 Chemical treatment liquid
50 Jig

The invention claimed is:

1. A method for producing a highly elastic stent the method comprising:
    inserting a rod-shaped core metal into a hollow portion of a tube-shaped stent base;
    maintaining, as needed, linearity of the stent base with the core metal inserted therein, and thereafter, cutting slot forming portions with a laser light while suppressing a heat effect by the laser light on a periphery of the slot forming portions so as to form slots and thus to make a stent; and
    removing the core metal from the stent, wherein
    at least a part of the highly elastic stent has such a property that load increases with displacement without exhibiting a distinct yield on a load-displacement curve obtained by a compression test and a bending test.

2. The method for producing the highly elastic stent according to claim 1, the method further comprising expanding the stent from which the core metal has been removed to a predetermined diameter while performing heat treatment on the stent at 350° C. or below.

3. The method for producing the highly elastic stent according to claim 1, wherein the slots are formed by cutting the slot forming portions with a laser that uses a water jet, which is formed so as to reach the stent base, as a waveguide of the laser light.

4. The method for producing the highly elastic stent according to claim 2, wherein the slots are formed by cutting the slot forming portions with a laser that uses a water jet, which is formed so as to reach the stent base, as a waveguide of the laser light.

5. A method for producing a highly elastic stent, the method comprising:
    inserting a rod-shaped core metal into a hollow portion of a tube-shaped stent base;
    maintaining, as needed, linearity of the stent base with the core metal inserted therein, and thereafter, cutting slot forming portions with a laser light while suppressing a heat effect by the laser light on a periphery of the slot forming portions so as to form slots and thus to make a stent; and
    removing the core metal from the stent, wherein
    at least a part of the highly elastic stent has such a property that load increases with displacement without exhibiting a distinct yield on a load-displacement curve obtained by a compression test and a bending test, and
    wherein the alloy is any of Ti—Ni alloy, Co—Cr alloy, and stainless alloy.

6. The method for producing the highly elastic stent according to claim 5, the method further comprising expanding the stent from which the core metal has been removed to a predetermined diameter while performing heat treatment on the stent at 350° C. or below.

7. The method for producing the highly elastic stent according to claim 5, wherein the slots are formed by cutting the slot forming portions with a laser that uses a water jet, which is formed so as to reach the stent base, as a waveguide of the laser light.

8. The method for producing the highly elastic stent according to claim 6, wherein the slots are formed by cutting the slot forming portions with a laser that uses a water jet, which is formed so as to reach the stent base, as a waveguide of the laser light.

9. A method of manufacturing a stent, comprising:
    inserting a rod-shaped core metal into a hollow portion of a tube-shaped stent base;
    maintaining, as needed, linearity of the stent base with the core metal inserted to the stent base;
    forming slots to make a stent by cutting slot forming portions with a laser light while suppressing a heat effect by the laser light on a periphery of the slot forming portions; and
    removing the core metal from the stent.

10. The method of manufacturing a stent according to claim 9, further comprising expanding the stent from which the core metal has been removed to a predetermined diameter while performing heat treatment on the stent at 350° C. or below.

11. The method of manufacturing a stent according to claim 9, wherein the slots are formed by cutting the slot forming portions with a laser that uses a water jet, which is formed so as to reach the stent base, as a waveguide of the laser light.

12. The method of manufacturing a stent according to claim 9, wherein the tube-shaped stent base is any one of Ti—Ni alloy, Co—Cr alloy and stainless alloy.

13. The method of manufacturing a stent according to claim 9, wherein the tube-shaped stent base is Mg alloy.

14. The method of manufacturing a stent according to claim 10, wherein the slots are formed by cutting the slot forming portions with a laser that uses a water jet, which is formed so as to reach the stent base, as a waveguide of the laser light.

15. The method of manufacturing a stent according to claim 10, wherein the tube-shaped stent base is any one of Ti—Ni alloy, Co—Cr alloy and stainless alloy.

16. The method of manufacturing a stent according to claim 10, wherein the tube-shaped stent base is Mg alloy.

17. The method of manufacturing a stent according to claim 11, wherein the tube-shaped stent base is any one of Ti—Ni alloy, Co—Cr alloy and stainless alloy.

18. The method of manufacturing a stent according to claim 11, wherein the tube-shaped stent base is Mg alloy.

19. The method of manufacturing a stent according to claim 14, wherein the tube-shaped stent base is any one of Ti—Ni alloy, Co—Cr alloy and stainless alloy.

20. The method of manufacturing a stent according to claim 14, wherein the tube-shaped stent base is Mg alloy.

\* \* \* \* \*